United States Patent
Coquerel et al.

(10) Patent No.: US 8,034,948 B2
(45) Date of Patent: Oct. 11, 2011

(54) METHOD FOR RESOLVING OMEPRAZOLE SALTS

(75) Inventors: Gérard Coquerel, Notre Dame de Bondeville (FR); Guillaume Tauvel, Rouen (FR); Marie-Noelle Petit, Mont Saint Aignan (FR)

(73) Assignee: Universite de Rouen, Mont-Saint-Aignan (FR)

( * ) Notice: Subject to any disclaimer, the term of this patent is extended or adjusted under 35 U.S.C. 154(b) by 645 days.

(21) Appl. No.: 12/201,144

(22) Filed: Aug. 29, 2008

(65) Prior Publication Data

US 2009/0124811 A1 May 14, 2009

(30) Foreign Application Priority Data

Aug. 29, 2007 (FR) ..................................... 07 06058

(51) Int. Cl.
*C07D 401/12* (2006.01)
(52) U.S. Cl. .................................................. 546/273.7
(58) Field of Classification Search ................ 546/273.7
See application file for complete search history.

(56) References Cited

U.S. PATENT DOCUMENTS

2006/0089386 A1    4/2006  Parthasaradhi Reddy et al.

FOREIGN PATENT DOCUMENTS

| EP | 1 595 879 A2 | 11/2005 |
|----|--------------|---------|
| WO | 98/54171 A | 12/1998 |
| WO | 2004/016569 A1 | 2/2004 |
| WO | 2004/063188 A1 | 7/2004 |
| WO | 2005/105786 A1 | 11/2005 |
| WO | 2006/003163 A1 | 1/2006 |
| WO | 2006/131338 A2 | 12/2006 |

*Primary Examiner* — Patricia Morris
(74) *Attorney, Agent, or Firm* — Young & Thompson

(57) ABSTRACT

The present invention relates to the resolution by preferential crystallization of potassium salts of racemic omeprazole which is a solvate of ethanol and/or of ethylene glycol, which consists in converting the omeprazole to the potassium salt in the form of a solvate or of a mixture of these solvates in the presence of an excess of inorganic base which is a source of potassium, the said potassium salts existing in the form of conglomerates, and in then resolving the said conglomerates, independently or simultaneously, by preferential crystallization in order to separate the two (S) and (R) enantiomers of these potassium salts of omeprazole.

11 Claims, 7 Drawing Sheets

METHOD FOR RESOLVING OMEPRAZOLE SALTS

FIELD OF INVENTION

The present invention relates to the field of the resolution of chiral compounds which exist in the form of two optical antipodes (enantiomers), such as omeprazole.

BACKGROUND OF THE INVENTION

More particularly, the invention relates to the preparation of the pure enantiomer (S)-(−)-omeprazole (esomeprazole), with the chemical name 5-methoxy-2-[(S)-[(4-methoxy-3,5-dimethyl-2-pyridinyl)methyl]sulphinyl]-1H-benzimidazole, and of its pharmaceutically acceptable alkali metal salts.

Very specifically, the present invention relates to the resolution of the potassium salts of racemic omeprazole by preferential crystallization and in particular by the AS3PC (Auto-Seeded Programmed Polythermic Preferential Crystallization) method.

Racemic omeprazole is represented by the following general formula (I):

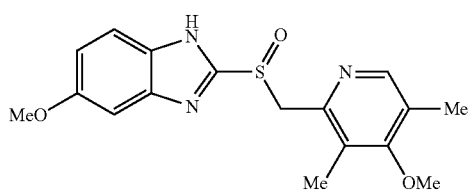
(I)

The invention relates both to the omeprazole of above formula (I) and to its tautomeric form, and likewise as regards its salts and enantiomers below.

The pure enantiomer (S)-omeprazole (esomeprazole) is represented by the following general formula (II):

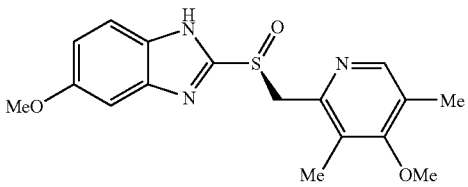
(II)

This pure enantiomer is sold as a drug in the form of the (S)-omeprazole magnesium salt trihydrate under the Nexium® name, represented by the following general formula (III):

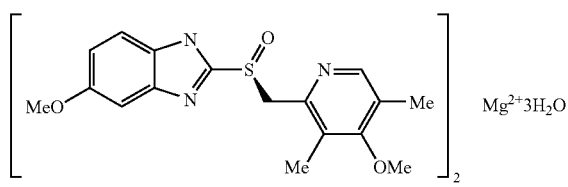
(III)

It may be remembered that the magnesium salt of the (S) enantiomer of omeprazole is the first proton pump inhibitor (PPI) developed and sold in the pure enantiomer form. Racemic omeprazole and esomeprazole are employed to treat gastric and/or duodenal ulcers. They can be used in the prevention and treatment of gastrointestinal disorders, gastro-oesophageal reflux, digestive tract hemorrhage and dyspepsia. Furthermore, (S)-omeprazole can be of use in the treatment of psoriasis and in the treatment of infections with the bacterium *Helicobacter pylori* and related pathologies.

Omeprazole and its enantiomers belong to the chemical class of the prazoles comprising a benzimidazole or imidazopyridine ring system. Mention may be made, among the many prazoles sold or in the course of clinical development, of: ilaprazole, lansoprazole, leminoprazole, pantoprazole and rabeprazole/pariprazole in their racemic and/or pure enantiomer form.

These prazoles, and more particularly their corresponding alkali metal or alkaline earth metal salts, are used as inhibitors of gastric acid secretion and as such in the treatments.

They are chiral sulphoxides, the sulphur atom of which, bonded on the one hand to an oxygen atom and on the other hand to heteroaromatic ring A and methylene-heteroaromatic ring B substituents which are different, constitutes the stereogenic centre.

They can be represented by the following general formula (IV):

(IV)

The change from omeprazole (racemic compound) to esomeprazole (pure laevorotatory (−) enantiomer of (S) absolute configuration) constituted, for this class of PPI pharmaceutical compounds, the first chiral switching. It has been shown that this compound, in its racemic form and each of its enantiomers, can exhibit different pharmacological and pharmacokinetic properties.

Omeprazole (racemic compound) was described for the first time in Patent EP 0 005 129 and some of its alkali metal salts in Patents EP 124 495 and U.S. Pat. No. 4,738,974.

The alkali metal and alkaline earth metal salts and more particularly the magnesium salt of omeprazole and those of other PPI prazoles have been shown to be stable and, in some cases, non hygroscopic.

A large number of documents of the prior art describe the preparation of esomeprazole and its alkali metal and alkaline earth metal salts.

Generally, these documents describe conventional methods which can be categorized according to the methods involved:

Erlandsson P. et al. published the first resolution of racemic omeprazole, carried out by chiral phase chromatography, in *J. Chromatogr.*, 1990, 532, 305-319.

Patent Applications DE 40 35 455 and WO 94/27988 describe the resolution of racemic omeprazole and similar prazoles of pyridinylmethylsulphinyl-1H-benzimidazole type by fractional crystallization of diastereomeric salts and/or reverse phase chromatographic separation of covalent diastereomeric ethers of the type of chiral N-acyloxymethyl bonded to the free nitrogen atom N of the benzimidazole ring, followed by basic hydrolysis.

Patent Application US 2006/0089386 describes the resolution of racemic omeprazole using (S)-camphor-sulphonyl chloride by formation of covalent diastereomers separated by fractional crystallization, followed by basic hydrolysis, to give (S)-omeprazole >99% ee.

Patent Application WO 96/01623 describes the formation of the magnesium salts of the (R)- and (S)-omeprazole enantiomers with an enantiomeric excess of 99% ee with the crystalline form I.

Patent Application WO 96/17077 describes a method for the stereoselective bioreduction of the sulphoxide (racemic omeprazole) to give the corresponding sulphide (thioether) using microorganisms, such as *Escherichia coli, Proteus mirabilis* or *Proteus vulgaris*, comprising the enzyme DMSO reductase, or using this purified enzyme. This enantioselective bioreduction leaves the omeprazole greatly enriched in (+) enantiomer with an enantiomeric excess of 99% ee. The (−) enantiomer is obtained with 70% ee.

Patent Application WO 96/17076 describes a method for the stereoselective biooxidation of the precursor sulphide (thioether) of omeprazole in the presence of microorganisms, such as *Penicillium frequentans, Brevibacterium paraffinolyticum* or *Mycobacterium* sp., to give the (S)-omeprazole enantiomer of 99% ee.

Patent Application WO 96/02535 describes the asymmetric synthesis involving asymmetric oxidation of the prochiral sulphide using the catalytic system $Ti(O-isoPr)_4$/diethyl D-tartrate/$H_2O$ in the presence of cumene hydroperoxide, of tertiary amine organic base and of organic solvent, such as toluene, followed by in situ formation of corresponding sodium salts. This catalytic process makes it possible to obtain chiral sulphoxides, in particular the sodium salt of (S)-omeprazole, of 99% ee.

Patent Application WO 2006/040635 describes the enantioselective synthesis of pyridinylmethylsulphinyl-benzimidazoles by catalytic oxidation of the corresponding precursor prochiral sulphide derivatives using the came catalytic system, $Ti(O-isoPr)_4$/diethyl D-tartrate/$H_2O$, cumene hydroperoxide and tertiary amine organic base, without addition of organic solvent, to give the (S)-omeprazole enantiomer and its alkali metal and alkaline earth metal salts, in particular its magnesium salt.

Patent Application WO 03/089408 describes the asymmetric synthesis of (S)-omeprazole by catalytic enantioselective oxidation of the precursor prochiral sulphide using a monodentate chiral ligand of methyl ester of L-mandelic acid type in the presence of cumene hydroperoxide and of $Ti(O-isoPr)_4$/ $H_2O$, and in situ preparation of the corresponding sodium salt of 99% ee.

Patent Application WO 98/28294 describes the preparation of solid (S)-omeprazole in an amorphous form, a crystalline form (denoted form A) or a partially crystalline form (denoted form B).

Patent Application WO 98/54171 describes the formation of the magnesium salts of the (S) and (R) enantiomers of omeprazole dihydrate in the crystalline forms A and B and of the trihydrate. This patent also describes the formation of the potassium salts of the (S) and (R) enantiomers of omeprazole.

Patent Application WO 00/44744 describes the formation of a novel potassium salt of (S)-omeprazole hydrate of form B.

Patent Application WO 2004/002982 describes the separation of racemic omeprazole into its pure enantiomers by formation of diastereomeric salts starting from the sodium salt of racemic omeprazole brought together with the coordinating agent diethyl D-tartrate/$Ti(iso-Pr)_4$ in acetone and complexing using L-mandelic acid.

The selective crystallization of the diastereomer comprising the (S)-omeprazole, followed by basic hydrolysis, gives the (S)-omeprazole magnesium salt trihydrate of 99% ee. The corresponding dihydrate is formed by controlled drying.

Patent Application WO 2004/046134 describes the preparation of (S)-omeprazole magnesium salt trihydrate of crystalline form II starting from the amorphous form of the same salt.

Patent Application WO 97/02261 (EP 1 498 416) describes the enantiomeric increase of mixtures of (S)/(R) enantiomers of omeprazole by selective precipitation of the corresponding racemic compound in acetone or acetonitrile solvents The filtrate gives, after evaporation, (S)-omeprazole of 98-99% ee.

In *J. Phys. IV*, 2004, 113, 11-15, Coquerel G. presents the rationale supporting the formation of the anticonglomerate (corresponding to racemic omeprazole) and its crystallization using binary phase diagrams (see FIG. 5*b* of this publication).

Patent Application WO 2004/089935 describes the preparation of a novel crystalline form of (S)-omeprazole magnesium salt trihydrate, known as H1, and the access to (S)-omeprazole magnesium salt hemihydrate and (S)-omeprazole magnesium salt monohydrate, each characterized by X-ray powder diffraction diagrams.

Patent Application WO 2006/001753 describes the preparation of (S)-omeprazole and sodium salts obtained in crystalline forms identified as C, E and H starting from the corresponding precursor potassium salt treated in a basic medium.

Patent Application WO 2006/003163 describes the preparation of novel crystalline forms of (S)-omeprazole which is a solvate of methanol, characterized by X-ray powder diffraction diagrams.

Patent Application WO 2006/134605 describes the formation of amorphous (S)-omeprazole hydrate and its conversion to the anhydride by resuspension in an organic solvent and filtering.

Patent Application WO 2004/076440 describes the I and II forms of (S)-omeprazole and its hydrates.

Patent Application WO 2004/020436 describes amorphous hydrates of the magnesium salt of (S)-omeprazole and their preparation.

Patent Application WO 2007/031845 describes the preparation of (S)-omeprazole magnesium salt trihydrate in two novel polymorphic crystalline forms G1 and G2 and the preparation of a corresponding amorphous form.

Patent Application. WO 2007/049914 describes the formation of an (S)-omeprazole strontium salt tetrahydrate in a crystalline form A and an amorphous form.

Deng J. et al., in *Tetrahedron: Asymmetry*, 2000, 11, 1729-1732, describe the resolution of racemic omeprazole by formation of inclusion complexes using (S)-(−)-2,2'-dihydroxy-1-1'-binaphthyl (BINOL), followed by crystallization and by chromatographic separation, to give (S)-omeprazole of 99% ee.

Patent Application WO 2007/074099 describes the resolution of racemic omeprazole by formation of inclusion complexes using the chiral ligand (S)-1,1,2-triphenyl-1,2-ethanediol. The complex of (S)-omeprazole and 2 equivalents of chiral ligand formed yields crystalline (S)-omeprazole of 99% ee.

While some of these methods are used on the industrial scale, regulatory change, in particular with regard to the safety and quality of pharmaceutical products, and also the economic impact of decisions of official health bodies in the direction of better control of the cost of treatments are forcing the development and the optimization of novel methods for the preparation of the (S)-omeprazole enantiomer and its salts of pharmaceutical interest.

Mention may be made, among the existing methods described in the above patents, without implied limitation, of a body of disadvantages commonly encountered and which are directly related to the use of these methods, it being possible for several of these disadvantages to be found in one and the same method:

In the case of the catalytic asymmetric synthesis involving catalysts of Ti(O-isoPr)$_4$, vanadium trioxide or tungsten acetylacetonate type, the presence of residual heavy metals.

The formation of the sulphone, corresponding to the complete oxidation of the sulphur atom, which can be obtained at up to 40% with respect to the (S)-omeprazole and which is difficult to separate by chromatography or recrystallization.

The need to undergo a stage of chromatographic separation and of enantiomeric purification by recrystallization when the asymmetric synthesis methods provide (S)-omeprazole with a chemical purity <90% and with an enantiomeric purity <95% ee.

The use of a chiral phase HPLC chromatographic separation/purification method for direct chromatographic methods without involving covalent diastereomers or salts.

In the case of insufficient structural purity (Coquerel G., The 'structural purity' of molecular solids—An elusive concept? *Chem. Eng. Process*, 2006, 45, 857-862), when the enantiomer obtained in its neutral form or in the form of an alkali metal or alkaline earth metal salt, in particular the magnesium salt, is a mixture of forms, of hydrates and/or of solvates of different stabilities.

The removal of residual microorganisms and enzymes in the case of bioconversions.

A specific aim of the present invention is to present a method for the preparation of the pure enantiomer (S)-omeprazole which does not exhibit the disadvantages described above.

This aim is achieved by virtue of the application of the preferential crystallization method to racemic omeprazole in the salt form. Thus, the invention relates very particularly to the application to potassium salts of racemic omeprazole of the resolution by preferential crystallization of each of its enantiomers, making it possible to obtain the eutomer (S)-omeprazole in an enantiomerically and chemically pure form.

In particular, the AS3PC preferential crystallization method has formed the subject of an entirely original development which excludes the restrictive use of crystallization seeds. This method is described, for example, in the following patents and patent applications FR 2 710 337, WO 95/08522, EP 0 720 595 and U.S. Pat. No. 6,022,409 and in G. Coquerel, *Preferential Crystallization* in *Topic in Current Chemistry, Novel Optical Resolution Technologies*, Springer, Berlin-Heidelberg, edited by K. Sakai, N. Hirayama and R. Tamura, 2007, 269, 1-51. This method is denoted "AS3PC" for "Auto-Seeded Programmed Polythermic Preferential Crystallization".

The preferential crystallization methods are based on the alternating crystallization of the two (R) and (S) enantiomers of the same racemic chemical entity crystallizing in the conglomerate form in a medium which can be a solvent or a mixture of solvents or a combination of constituents including the solvent or solvents, this being the case for a given temperature range ΔT. Within this temperature range, this racemic mixture, in thermodynamic equilibrium with its saturated solution, is composed of two types of crystals each comprising only molecules with the same absolute configuration. Each enantiomer may incorporate molecules of solvent (solvates) and/or of water (hydrates).

SUMMARY OF THE INVENTION

The knowledge of these (R) enantiomer-(S) enantiomer-medium heterogeneous equilibria provides information taken advantage of in carrying out an efficient resolution by preferential crystallization.

The studies carried out by the Applicant Company show that racemic omeprazole is not a conglomerate. This means that the AS3PC preferential crystallization method or any other preferential crystallization method cannot be applied. It is the same for the sodium and magnesium salts.

On the other hand, entirely unexpectedly, the Applicant Company has found that the potassium salts of racemic omeprazole in the form of ethanol or ethylene glycol solvates are conglomerates without detectable solid solution. The possible range of miscibility in the solid state would be less than 1%, as illustrated in FIG. 1.

Thus, surprisingly, the potassium salts of racemic omeprazole, of a mixture enriched in the (S) enantiomer of omeprazole or of the pure enantiomer (S)-omeprazole are stable in the presence of an excess of potassium hydroxide in mixtures of alcohol/alcohol or alcohol/water solvents or pure alcohol. Under these concentration and temperature conditions, these potassium salts exhibit an incongruent solubility (G. Coquerel in *Preferential Crystallization*, in *Topic in Current Chemistry*, Novel Optical Resolution Technologies, Springer, Berlin-Heidelberg, edited by K. Sakai, N. Hirayama and R. Tamura, 2007, 269, 1-51). This means that, in order to quantitatively obtain this salt with an enantiomeric excess of greater than 99% ee, it is necessary to operate in an alcoholic medium with an excess of potassium hydroxide.

Thus, the invention relates to a method for the resolution of racemic omeprazole, characterized in that racemic omeprazole is converted to its potassium salt in the solvate form in the presence of an excess of inorganic base which is a source of potassium, the said potassium salt of racemic omeprazole in the solvate form existing in the form of conglomerates, the partial solid solution regions of which, if they exist, are less than 1%, and then in that the said conglomerates are resolved by preferential crystallization in order to separate the two (S) and (R) enantiomers of the said potassium salt of omeprazole.

In the above method, the solvate of the potassium salt of racemic omeprazole is chosen from the ethanol solvate or the ethylene glycol solvate or a mixture of these.

The resolution of the conglomerates according to the invention is carried out by seeded or auto-seeded preferential crystallization.

A first embodiment of the invention is a method for the resolution by non-auto-seeded (i.e. seeded) preferential crystallization of a salt of racemic omeprazole; this method comprises the following stages:

a) a first homogeneous solution is prepared which is composed of the racemic mixture in the conglomerate form and of an excess of the first enantiomer to be recovered in the form of a solvate of the potassium salt of (X)-omeprazole, denoted X—K-solvate, where X represents the (R) or (S) enantiomer, and of a medium, the representational point I of which (FIG. 2), defined by the variables of concentration and temperature $T_I (T_I > T_{HOMO})$, lies within the single-phase region composed of the undersaturated solution;

b) a cooling programming law is applied to the single-phase mixture;

c) when the mixture reaches a temperature below the temperature $T_{HOMO}$, the solution is seeded with enantiomerically pure seeds of the first X—K-solvate enantiomer to be recovered;

d) throughout the duration of the crystal growth, a stirring rate which gently increases as a function of the time is adjusted so that it is sufficiently slow to promote growth of the first X—K-solvate enantiomer;

e) the crystals of the first X—K-solvate enantiomer are harvested;

f) the same weight of racemic mixture as the weight of the crystals harvested in the preceding stage is added to the mother liquors and the new combination is brought to the temperature $T_I$ ($T_I > T_{HOMO}$), the point I' lying in the single-phase region (this point I' corresponds to the symmetry of the point I with respect to the plane of identical composition, by moles or by weight, of the two enantiomers);

g) the same cooling programming law as in stage (b) is applied to the single-phase mixture prepared in stage (f) comprising the second enantiomer, so that the mother liquors retain a slight supersaturation during the crystallization in order to favour the growth of the second X—K-solvate enantiomer during the seeding;

h) when the mixture reaches a temperature below the temperature $T_{HOMO}$, the solution is seeded with enantiomerically pure seeds of the second X—K-solvate enantiomer;

i) throughout the duration of the crystal growth of the preceding stage, a stirring rate which gently increases as a function of the time is adjusted so that it is sufficiently slow to promote the growth of this second X—K-solvate enantiomer;

j) the crystals of the second X—K-solvate enantiomer are harvested;

k) the same weight of racemic mixture as the weight of the crystals harvested in the preceding stage is added to the mother liquors in order to obtain a solution having an identical composition to that of the initial solution;

l) stages (a) to (k) are repeated in order to successively obtain one and then the other of the two enantiomers.

In stage (a) of the above method, the medium is composed of an alcoholic solvent or mixture of alcoholic solvents, water and an excess of potassium hydroxide.

According to a second embodiment of the invention, the method for the resolution of the conglomerates can be carried out by preferential crystallization and very particularly by the AS3PC, "Auto-Seeded Programmed Polythermic Preferential Crystallization", method. Thus, a method for AS3PC resolution of a salt of racemic omeprazole according to the invention comprises the following stages:

a) a first combination is prepared which is composed of the racemic mixture in the conglomerate form, of the first enantiomer to be recovered, in the form of a solvate of the potassium salt of (X)-omeprazole, denoted X—K-solvate, where X represents the (R) or (S) enantiomer, and of a medium, the representational point E of which (FIG. 2a), defined by the variables of concentration and temperature $T_B$, lies within the two-phase region composed of crystals of X—K-solvate and of its saturated solution (this point E' corresponds to the symmetry of the point E with respect to the plane of identical composition, by moles or by weight, of the two enantiomers);

b) a cooling programming law is applied to the two-phase mixture, such that the mother liquors retain a slight supersaturation which favours the growth of the first X—K-solvate enantiomer present in the form of crystals, while preventing the spontaneous nucleation of the second X—K-solvate enantiomer dissolved in the solution;

c) throughout the duration of the crystal growth, a stirring rate which gently increases as a function of the time is adjusted so that it is sufficiently slow to promote growth of the first X—K-solvate enantiomer, while avoiding the generation of uncontrolled nucleation and the attrition of crystals;

d) the crystals of the first X—K-solvate enantiomer are harvested;

e) the same weight of racemic mixture as the weight of the crystals harvested in the preceding stage is added to the mother liquors and the new combination is brought to the temperature $T_B$, the point E' lying in the two-phase region of the second X—K-solvate enantiomer in excess, in equilibrium with its saturated solution;

f) the same cooling programming law as in stage (b) is applied to the two-phase mixture prepared in stage (e) comprising the second X—K-solvate enantiomer, so that the mother liquors retain a slight supersaturation during the crystallization, in order to favour the growth of the second X—K-solvate enantiomer present in the form of crystals, while preventing the spontaneous nucleation of the first X—K-solvate enantiomer present in the solution;

g) throughout the duration of the crystal growth of the preceding stage, a stirring rate which gently increases as a function of the time is adjusted so that it is sufficiently slow to promote the growth of this second X—K-solvate enantiomer while avoiding the generation of uncontrolled nucleation and the attrition of crystals;

h) the crystals of the second X—K-solvate enantiomer are harvested;

i) the same weight of racemic mixture as the weight of the crystals harvested in the preceding stage is added to the mother liquors in order to obtain a combination having an identical composition to that of the initial combination E;

j) stages (a) to (i) are repeated in order to successively obtain one and then the other of the two enantiomers.

In stage (a) of the above method, the medium is composed of an alcoholic solvent or mixture of alcoholic solvents, water and an excess of potassium hydroxide.

The method of the invention in its various embodiments is simple, economic and easy; it does not require the use of chiral intermediates of organic or organometallic type and/or of resolving agents used in the form of salts or of covalent diastereomers or of microorganisms which are appropriate.

In the medium, the solvent or mixture of solvents is of alcoholic type and is preferably chosen from ethanol or ethylene glycol, pure or in the presence of water, with an excess of potassium hydroxide.

Advantageously, in the process of the invention, the racemic mixture, equimolar mixture of the enantiomers, in the medium used is, for the temperature range $T_B$-$T_F$ or $T_{HOMO}$-$T_F$, a conglomerate.

According to a useful characteristic, the mixture to be resolved is stable in this medium and in the temperature range used between $T_B$ and $T_F$ or $T_{HOMO}$-$T_F$.

In the method of the invention, the temperature $T_L$ corresponds to the dissolution temperature of the racemic mixture alone, the temperature $T_{HOMO}$ corresponds to the homogenization temperature of the solution enriched in one of the enantiomers, the temperature $T_I$ corresponds to the initial temperature of the seeded preferential crystallization method such that $T_I > T_{HOMO}$ and the temperature $T_B$ corresponds to the initial temperature of the AS3PC preferential crystallization method such that $T_L < T_B < T_{HOMO}$. The knowledge of the supersaturation capabilities of the solutions between $T_L$ and $T_F$ is also of use, according to the cooling kinetics. The time of appearance of the crystals by primary nucleation in the homogeneous racemic solution L (cf. FIGS. 1, 2, 2a and 3), cooled starting from a temperature slightly greater than $T_L$ with the same kinetics, gives an indication with regard to the supersaturation capacity tolerated by the conglomerate under these experimental conditions.

In the method of the invention, it is also beneficial to know the kinetics of the dissolution of a known weight of racemic mixture (of given particle size) dispersed in the solution at the temperature $T_B$.

In the method of the invention, the systems employed (stage (a)) are chosen from:

quinary systems [$K_2O$-EtOH—$H_2O$-(−)-omeprazole-(+)-omeprazole] and [$K_2O$-ethylene glycol-$H_2O$-(−)-omeprazole-(+)-omeprazole];

a senary system [$K_2O$-EtOH-ethylene glycol-$H_2O$-(−)-omeprazole-(+)-omeprazole];

ternary systems, by classification of the quinary systems as ternary systems comprising the constituents: alcohol(s) (ethanol and/or ethylene glycol), water and excess of potassium hydroxide in the medium.

For the senary system, this simplification is not possible but it is possible to consider juxtaposed ternary systems giving rise to preferential cocrystallization.

The various crystalline or amorphous forms are determined using an analytical method such as X-ray powder diffraction (XRPD). This method, which is well known to a person skilled in the art, is capable of producing a qualitative analysis of the forms possibly present in the same solid sample, except for the amorphous phases.

The resolution by preferential crystallization was studied systematically in ethanol and in ethanol/water and ethanol/ethylene glycol mixtures using the AS3PC method as restated above and described in detail in WO 95/08522. It was also studied in the ethanol/water azeotropic mixture using the seeded method.

Each potassium salt of omeprazole solvated with ethanol or ethylene glycol was characterized by X-ray powder diffraction. The diffractograms (XRPD) of these racemic and enantiomerically pure phases are presented respectively in FIGS. 4 and 5.

Furthermore, the potassium salt of omeprazole ethanol solvate was characterized by single-crystal X-ray diffraction.

The positions and the relative intensities of the characteristic peaks for the ethanol solvate of the potassium salt of racemic omeprazole and for the ethanol solvate of the potassium salt of enantiomerically pure (S)-omeprazole are shown in Table I below.

TABLE I

| Ethanol solvate of the potassium salt of racemic omeprazole | | Ethanol solvate of the potassium salt of (S)-omeprazole | |
|---|---|---|---|
| Angle 2-Theta (2θ) | Intensity I/Io % | Angle 2-Theta (2θ) | Intensity I/Io % |
| 6.42 | 100 | 6.37 | 100 |
| 11.22 | 5 | 11.17 | 10.4 |
| 14.11 | 6.5 | 14.07 | 14.2 |
| 14.89 | 21.4 | 14.88 | 24.3 |
| 16.12 | 9.3 | 16.04 | 15.6 |
| 16.41 | 8 | 16.34 | 16.3 |
| 18.12 | 10.5 | 18.09 | 21.5 |
| 18.93 | 5.2 | 18.87 | 16.5 |
| 20.09 | 9 | 20.08 | 17.7 |
| 22.24 | 4.1 | 22.19 | 12.9 |
| 23.11 | 11 | 23.06 | 15.3 |
| 24.05 | 14 | 23.99 | 26.1 |
| 24.53 | 11.9 | 24.51 | 17.6 |
| 25.20 | 6.2 | 25.16 | 15.4 |
| 25.86 | 5.9 | 25.8 | 16 |
| 27.14 | 12.5 | 27.06 | 17.9 |

It should be noted that, after several weeks, the ethanol solvate of the potassium salt of omeprazole tends, under an ambient atmosphere, to be converted to the potassium salt of (S)-omeprazole dihydrate.

However, these ethanol solvates of the potassium salt of racemic omeprazole and of (S)-omeprazole are stable in an ethanol-water mixture, in which ethanol predominates, and with an excess of potassium hydroxide.

The positions and the relative intensities of the characteristic peaks for the ethylene glycol solvate of the potassium salt of racemic omeprazole and for the ethylene glycol solvate of the potassium salt of enantiomerically pure (S)-omeprazole are shown in Table II below.

TABLE II

| Ethylene glycol solvate of the potassium salt of racemic omeprazole | | Ethylene glycol solvate of the potassium salt of (S)-omeprazole | |
|---|---|---|---|
| Angle 2-Theta (2θ) | Intensity I/Io % | Angle 2-Theta (2θ) | Intensity I/Io % |
| 6.67 | 100 | 6.63 | 100 |
| 10.99 | 4.7 | 10.96 | 1.7 |
| / | / | 12.99 | 0.7 |
| / | / | 14.52 | 1.3 |
| 15.75 | 5.1 | 15.67 | 3.2 |
| 16.04 | 6.1 | 16.03 | 1.4 |
| 17.98 | 17 | 18.03 | 1.3 |
| 20.20 | 6.1 | 20.20 | 4.2 |
| 22.07 | 5.5 | 21.92 | 1.2 |
| / | / | 22.41 | 1.1 |
| 24.08 | 5.1 | 24.09 | 3.1 |
| / | / | 24.33 | 1.4 |
| / | / | 24.60 | 2.7 |
| 24.80 | 7.4 | 24.84 | 2.2 |
| / | / | 25.07 | 1.7 |
| / | / | 26.17 | 1.1 |
| / | / | 26.95 | 2.4 |
| 28.49 | 5.7 | 28.55 | 0.9 |
| 29.28 | 4.1 | 29.27 | 0.9 |

As the method of the invention also results in the (R) enantiomer being obtained, the latter can be recycled according to the following stages:

i) Reduction of this chiral (R) sulphoxide to the achiral sulphide (thioether). This reduction is advantageously carried out according to the mild operating conditions described in the review by Madesclaire M, Tetrahedron, 1988, 44, 6537-6580, such as the reaction of Allenmark S., Acta. Chem. Scand., 1966, 20, 910-911, or in WO 2004/016569, ii) Oxidation of the sulphur atom of this sulphide to give racemic sulphoxide, using aqueous hydrogen peroxide solution or hypochlorite ion or perbenzoic acid or any other oxidizing agent, while avoiding the formation of sulphone.

The racemic omeprazole thus obtained can then be subjected to the preferential crystallization as described above.

BRIEF DESCRIPTION OF THE DRAWINGS

Other advantages and characteristics of the invention will become apparent from the examples which follow, in which reference will be made to the appended figures, where.

In this figure, the isoplethal vertical section comprising the S—K-solvate segment and the composition $X_E$ is represented.

Figure 1:
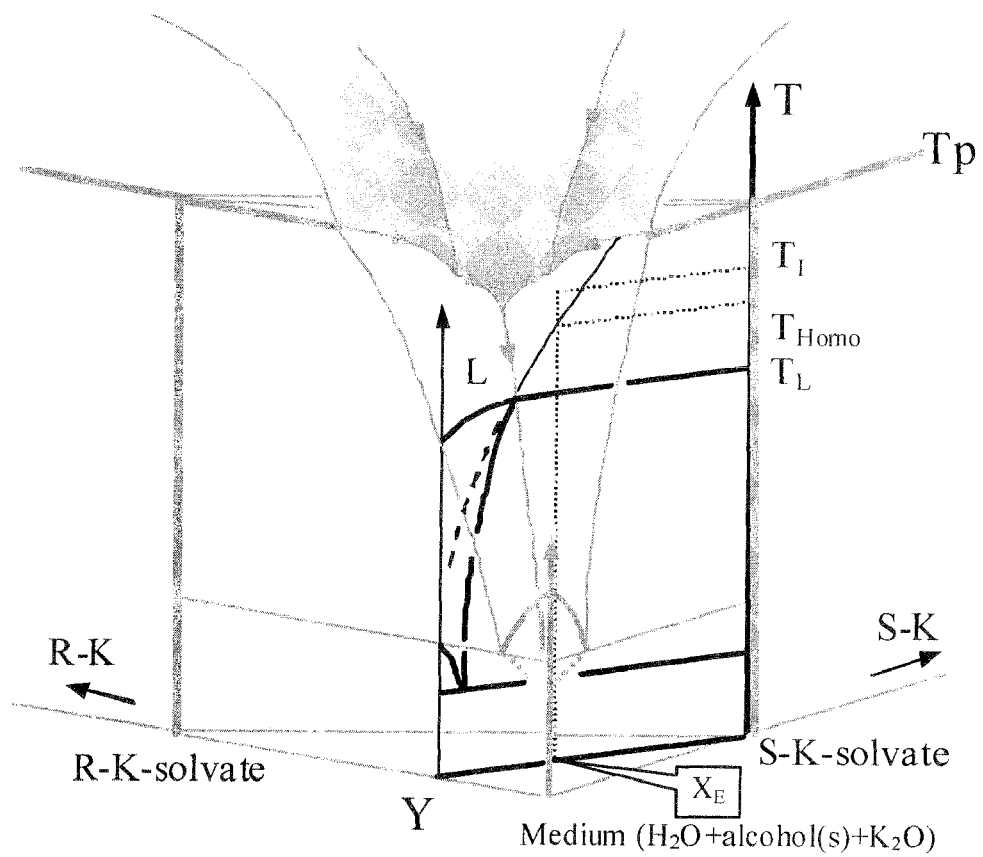
FIG. 1 is a representation in perspective of a portion of the polythermic ternary system: medium-(R) enantiomer-(S) enantiomer, and of the crystallization sheets of each constituent and of the compositions of the doubly saturated solutions (monovariant curves).
Figure 2:
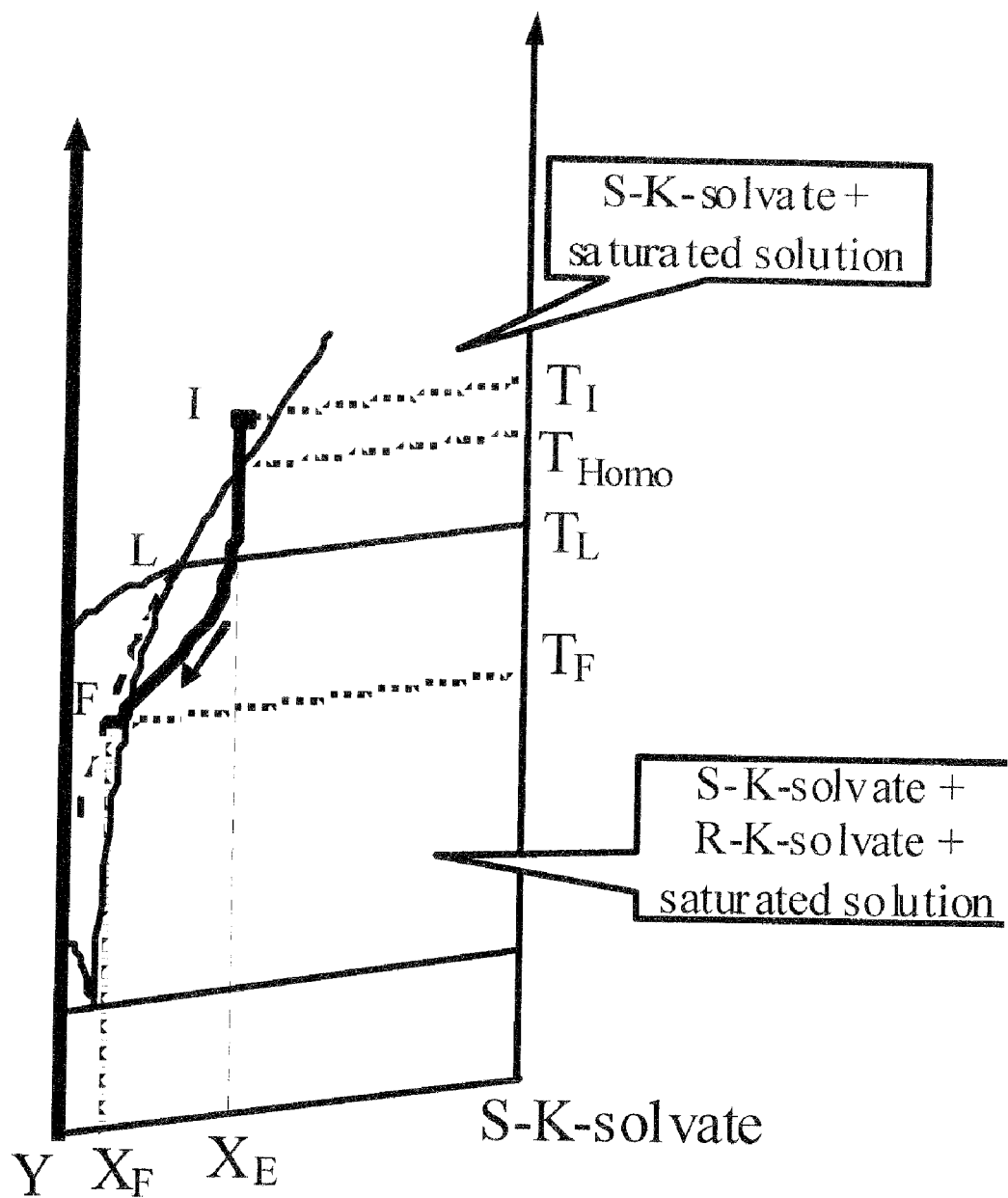

FIG. 2 is the polythermic isoplethal vertical section extracted from FIG. 1 (with the same symbols). It details the course of the solution point (as a bold line) from I to F during the resolution by seeded preferential crystallization.

Figure 2A:
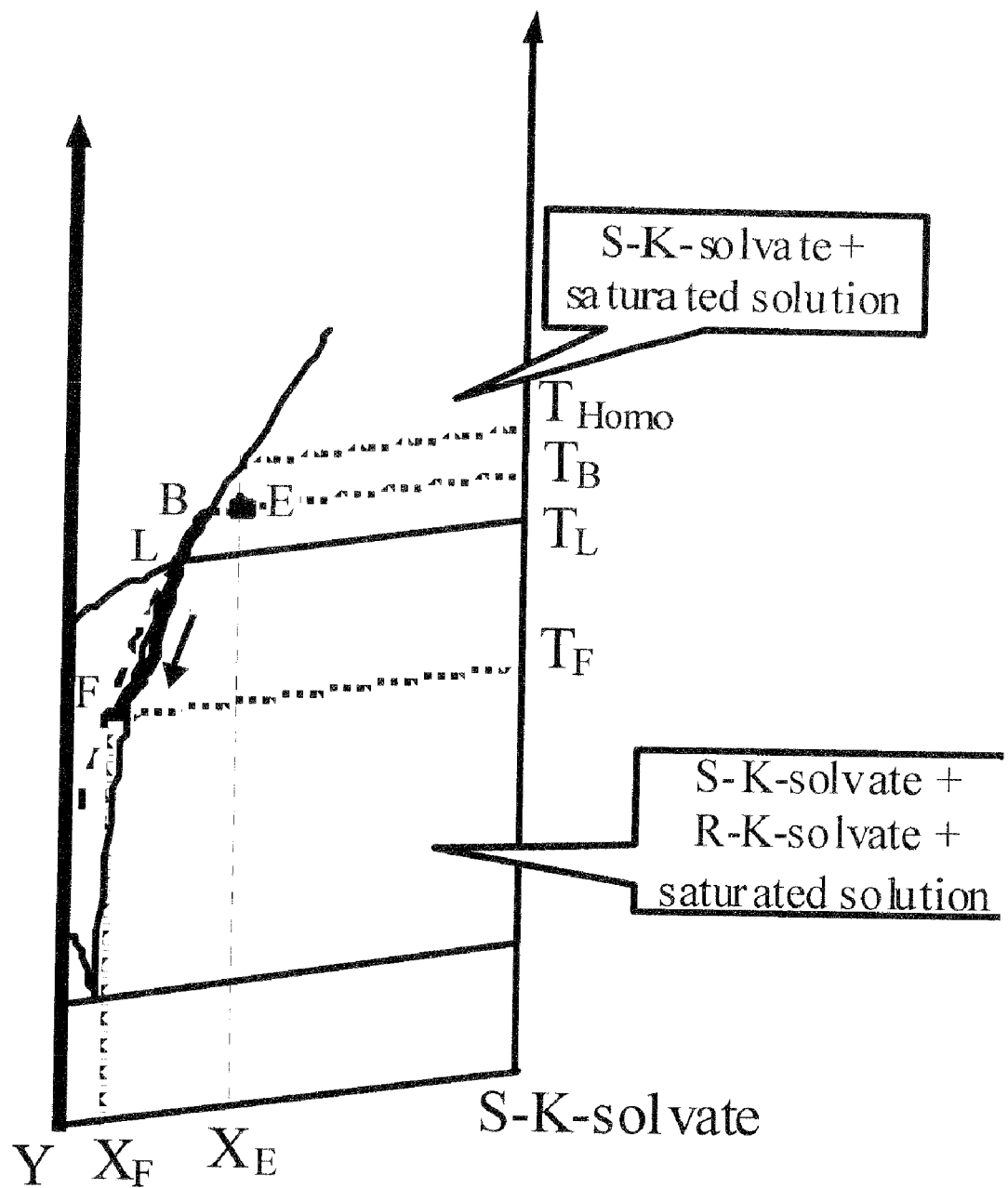

FIG. 2a is the polythermic isoplethal vertical section extracted from FIG. 1 (with the same symbols). It details the course of the solution point (as a bold line) from B to F during the resolution by the auto-seeded method: AS3PC.

Figure 3:
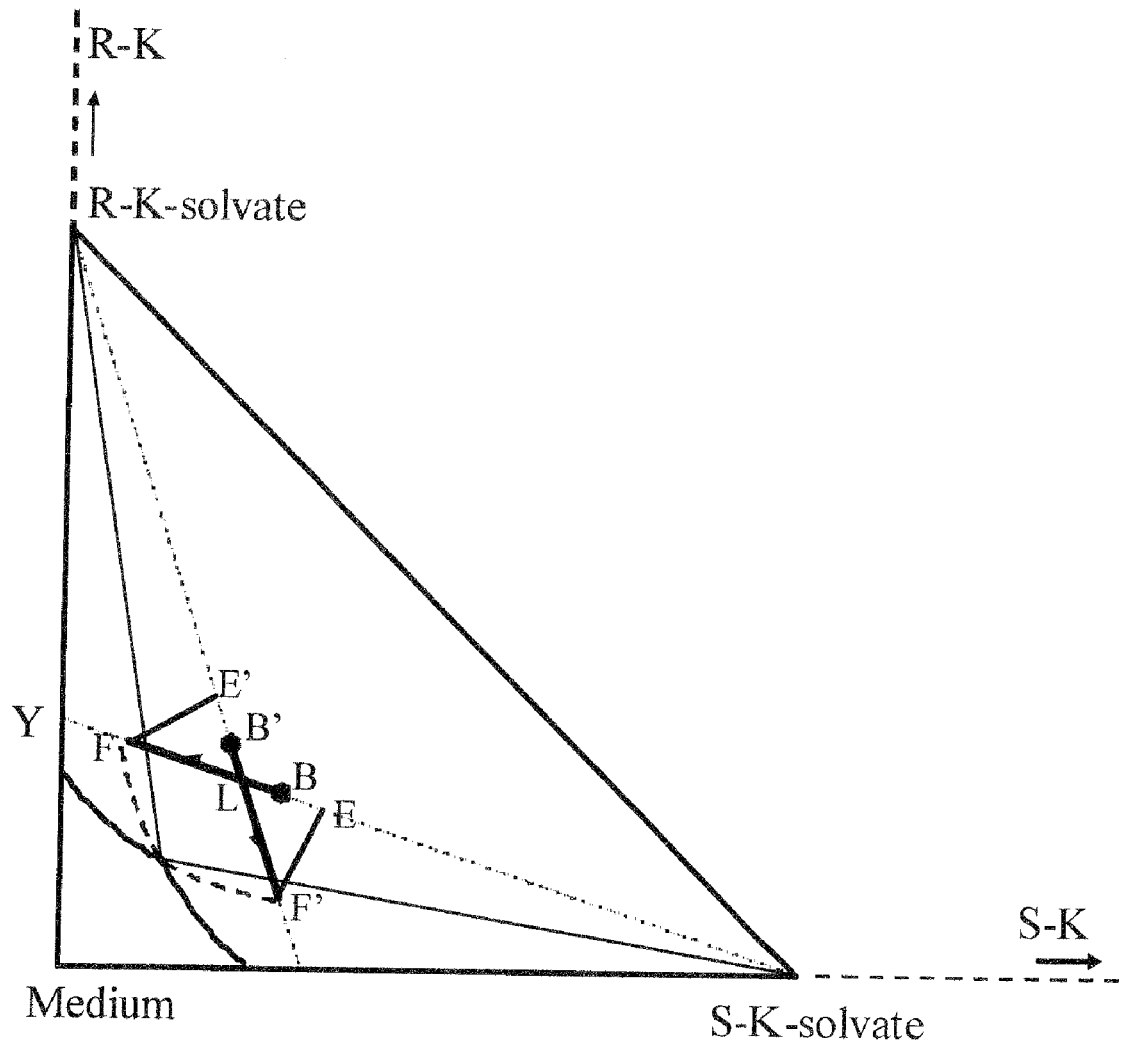

FIG. 3 is a projection onto the plane of the concentrations of the course of the solution point (as a bold line) during the resolution by the AS3PC method of the invention. The S—K-solvate—Y polythermic section of FIG. 2 is represented by the S—K-solvate—Y segment.

Figure 4:
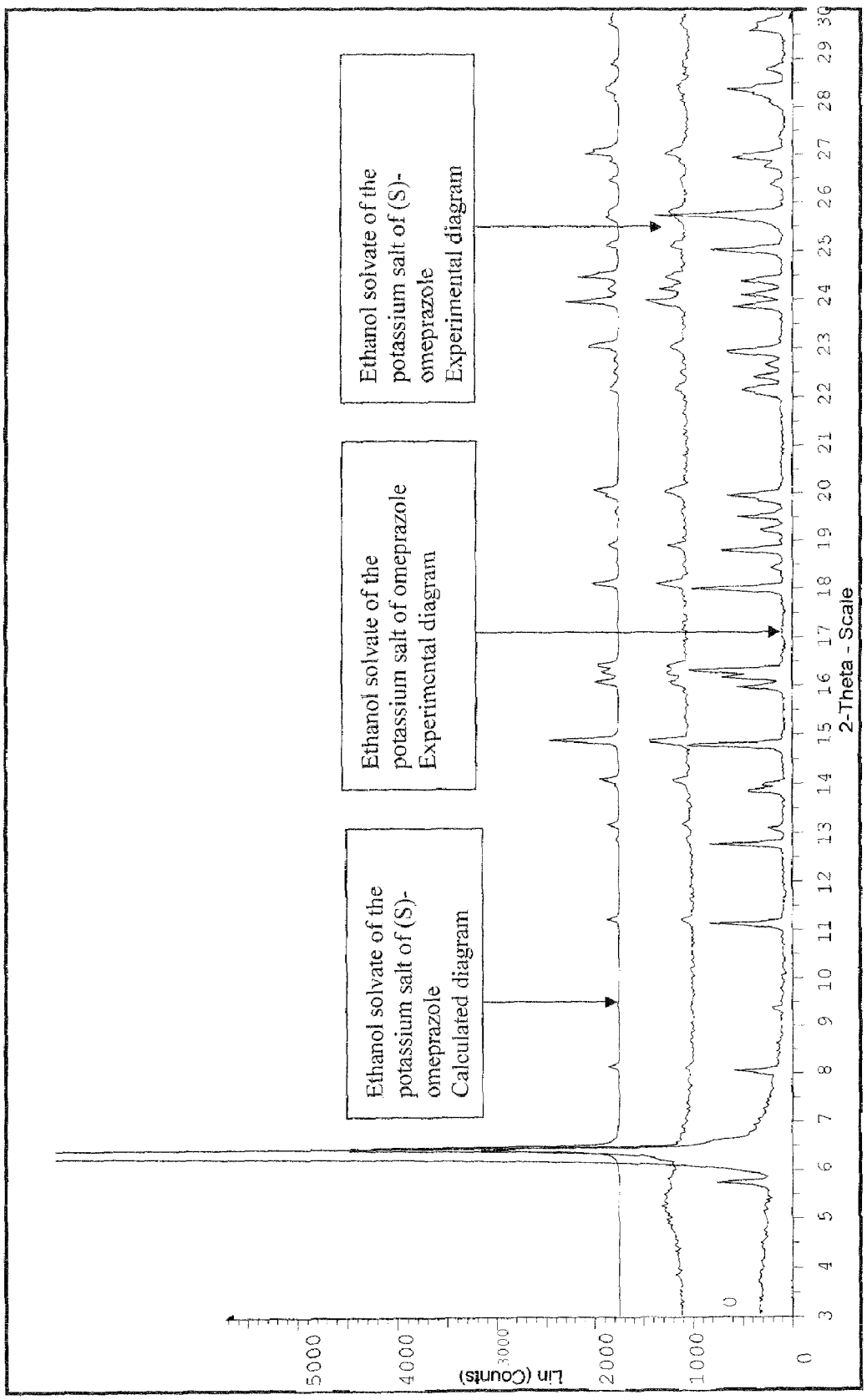

FIG. 4 shows the calculated and experimental diffractograms of the ethanol solvate of the potassium salt of (S)-omeprazole and that of the ethanol solvate of the potassium salt of racemic omeprazole.

Figure 5:
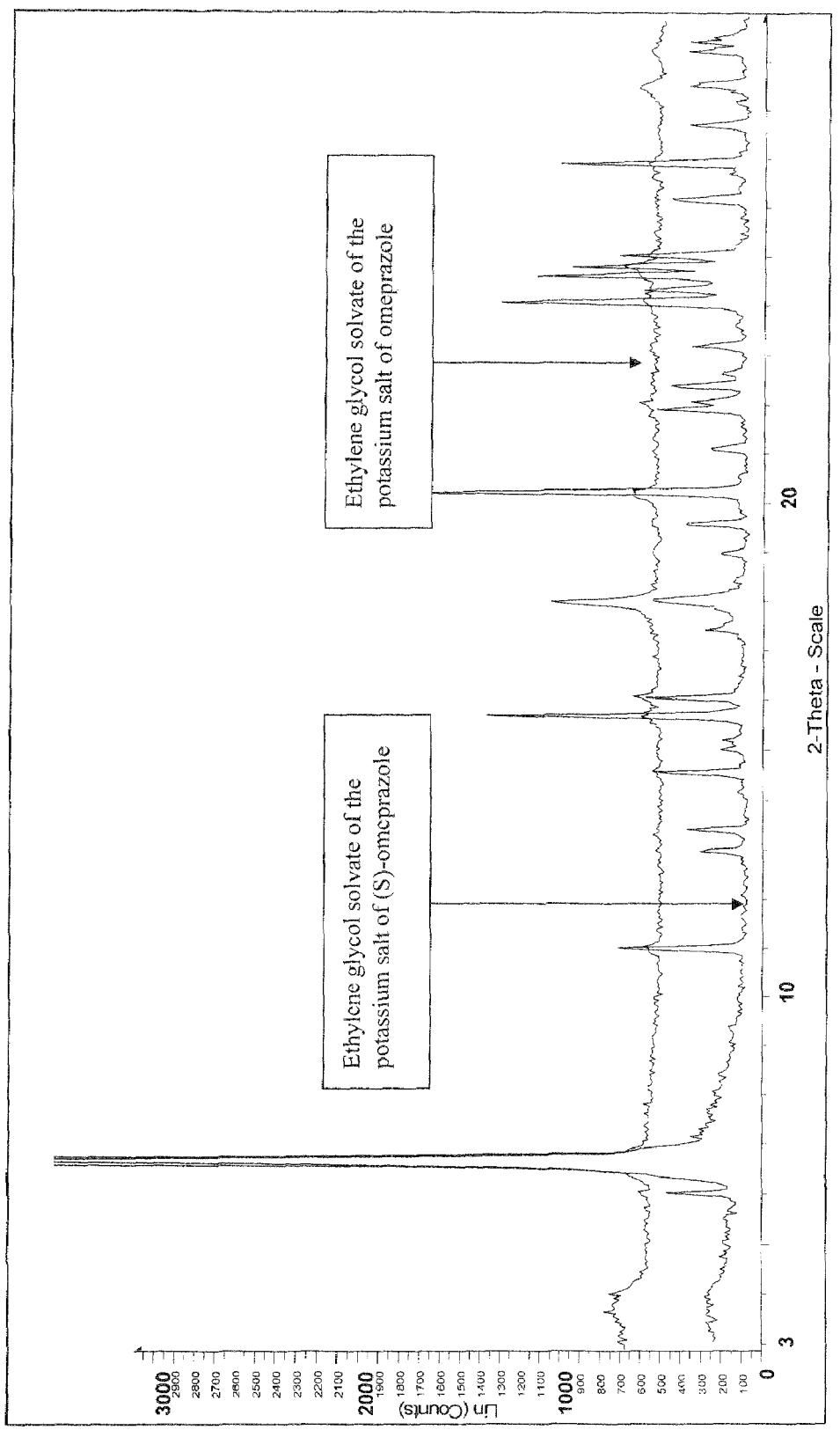

FIG. 5 shows the diffractograms of the ethylene glycol solvate of the potassium salt of racemic omeprazole and of (S)-omeprazole.

Figure 6:
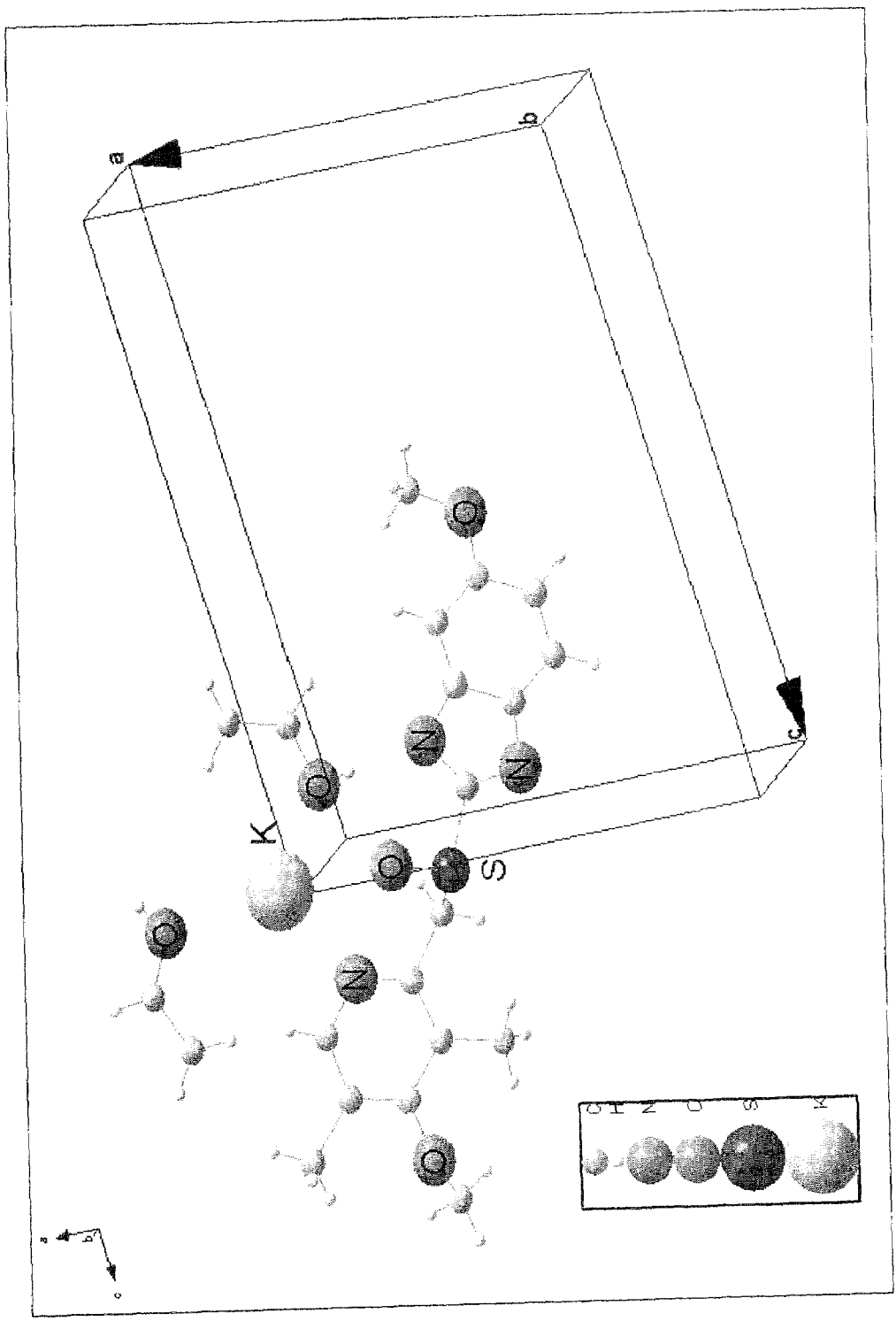

FIG. 6 shows the 3D representation of the asymmetric unit of the ethanol solvate of the potassium salt of (S)-omeprazole.

DETAILED DESCRIPTION OF THE INVENTION

Analytical Methods Used

Determination of the Enantiomeric Excess (% ee)

The enantiomeric excesses are determined by chiral HPLC chromatography using a ChiralPAK AD column (dimensions 250 mm×4.6 mm). The experimental conditions are:

| | |
|---|---|
| Solvent: | 100% absolute ethanol |
| Flow rate: | 1 ml·min$^{-1}$ |
| Detector: | λ = 302 nm |
| Injection: | 20 μl |
| Concentration: | approximately 0.4 g·l$^{-1}$ in ethanol |
| Retention time of the (−) enantiomer: | 8.1 minutes. |

Analyses by X-Ray Powder Diffraction

The X-ray powder diffraction (XRPD) analyses were carried out using a Bruker D5000 Matic diffractometer under the following conditions:

Copper anticathode, voltage 40 kV, intensity 40 mA
Ambient temperature
Range of measurements: 30 to 30°
Incrementation between each measurement: 0.04°
Measurement time per step: 4 s.

Solubility Measurements

The solubility measurements are calculated, for a given temperature and for a given excess of potassium hydroxide, in the following way:

$$\frac{\left(\begin{array}{c}\text{weight of omeprazole} \times \\ \text{molar mass of the solvate} \\ \text{of the potassium salt of omeprazole} \\ \hline \text{molar mass of omeprazole}\end{array}\right)}{\text{weight of omeprazole} + \text{weight of potassium hydroxide} + \text{weight of solvent} + \text{weight of water}}$$

Experimental Device

The operations are carried out alternately in two tubes with ground-glass necks (29/32), except on the 2 liter scale, that is to say for Examples 5 and 6. These tubes measure 19 cm in height and 45 mm in diameter for Examples 1, 2, 3, 4 and 7 and approximately 12 cm in height and 29 mm in diameter for Example 8. These tubes are provided, in their top part, with a side tube for establishing a negative pressure necessary for the filtration. The crystals are recovered on sintered glass No. 2 or 3, or on a Büchner funnel, which can be fitted to each tube via a rubber ring. Stirring is provided by a magnetic bar. The mother liquors pass successively from one tube to the other.

These transfers, reduced to the minimum, do not prevent losses in each operation. In order to compensate for these losses, two compensating actions are thus carried out:

for the losses of mother liquor, on the sintered glass and in the initial tube, this compensating is carried out by addition of racemic crystals and of solvent, so that this addition corresponds to the mixture L, for the losses of solvent, mainly due to the filtration caused by negative pressure, the compensating takes place by addition of additional solvent at each operation.

For a very volatile solvent, the compensating process is refined. A small amount of the solution is withdrawn, in order to determine the composition thereof, subsequently making possible the rigorous compensation.

In order to obtain good reproducibility of the results, the heat-exchange fluid circulating in the jacket of each crystallization chamber is temperature-regulated with an accuracy of ±0.1° C. The apparatus employed makes it possible to set a reproducible cooling law. These crystallization chambers are thermostatically controlled using a jacketed thermostat (LAUDA RE107).

In Examples 5 and 6, the operations are carried out in a jacketed 2 liter reactor thermostatically controlled by a thermostat (Huber CC 415) and equipped with a bottom valve. Stirring is mechanical and is provided by means of a double propeller blade. Filtration takes place by means of a centrifuge (Rousselet-Robatel RA20) at 5000 revolutions/min equipped with a basket with a diameter of 20 cm and a height of 10 cm and having a pore diameter of the nylon filtering media of 20 μm. The mother liquor recovered is decanted into the reactor for the following preferential crystallization.

It should be noted that the compensations after each operation are carried out by adding racemic omeprazole and potassium hydroxide (KOH); this results in shifting the composition of the mixture by formation of water resulting from the salification.

Example 1

Resolution in the Ethanol/Water Azeotropic Mixture by Seeded Preferential Crystallization Conditions Related to the Equilibria:

Solubility of the racemic mixture in the ethanol/water azeotropic mixture comprising 1.2 molar equivalents of potassium hydroxide (i.e., an excess of potassium hydroxide of 0.2 equivalent)

Coordinates of the point L: 9.1% by weight; temperature $T_L$: 31° C.

| Temperature (° C.) | 29 | 31 | 35 |
|---|---|---|---|
| Solubility (% by weight) | 8.7 | 9.1 | 13.7 |

Change in $T_{HOMO}$ with the enantiomeric excess:

| % (−) enantiomer | 0 | 3 | 6 | 9 |
|---|---|---|---|---|
| $T_{HOMO}$ (° C.) | 31 | 32 | 33 | 34 |

Conditions Related to the Kinetics:
Temperature $T_I$: 35° C.
Temperature $T_F$: 18° C.
Seeding temperature

| Entrainment No. | Seeding temperature (° C.) | Weight of the seeding (mg) |
|---|---|---|
| 1 | 19.7 | 95 |
| 2 | 27.2 | 99 |
| 3 | 27.2 | 99 |
| 4 | 28.3 | 97 |

Cooling kinetics: T=f(t):

| t (min) | 0 | 15 | 30 | 45 |
|---|---|---|---|---|
| T (° C.) | 35 | 29 | 24 | 18 |

Initial Conditions:
Initial enantiomeric excess: 9% ee.

| Weight of ethanol (g) | Weight of water (g) | Weight of (±) (g) | Weight of (−) (g) | Weight of potassium hydroxide (g) |
|---|---|---|---|---|
| 153.6 | 6.4 | 11.68 | 1.15 | 2.46 |

Results:
Filtration through a Büchner funnel (diameter 5 cm, double filter paper)

| Entrainment No. | Weight of pure enantiomer* (g) | Equivalent weight of (S)-omeprazole (g) | Enantiomeric excess (% ee) |
|---|---|---|---|
| 1 | 4.2 | 3.1 | (−) 93.2 |
| 2 | 6.8 | 4.9 | (+) 93.3 |
| 3 | 7.6 | 5.5 | (−) 91.7 |
| 4 | 7.5 | 5.4 | (+) 96.5 |

*The pure enantiomer corresponds to the ethanol solvate of the potassium salt of (S)-omeprazole Mean enantiomeric excess: 93.6% ee.

Example 2

Resolution in the Ethanol/Water Azeotropic Mixture by Auto-Seeded Preferential Crystallization Conditions Related to the Equilibria:
Solubility of the racemic mixture in the ethanol/water azeotropic mixture comprising 1.2 molar equivalents of potassium hydroxide (i.e., an excess of potassium hydroxide of 0.2 equivalent)
Coordinates of the point L: 8.7% by weight; temperature $T_L$: 29° C.

| Temperature (° C.) | 29 | 31 | 35 |
|---|---|---|---|
| Solubility (% by weight) | 8.7 | 9.1 | 13.7 |

Change in $T_{HOMO}$ with the enantiomeric excess:

| % (−) enantiomer | 0 | 3 | 12 |
|---|---|---|---|
| $T_{HOMO}$ (° C.) | 29 | 30 | 33 |

Conditions Related to the Kinetics:
Temperature $T_B$: 30° C.
Temperature $T_F$: 18° C.
Cooling kinetics: T=f(t):

| t (min) | 0 | 15 | 30 | 45 |
|---|---|---|---|---|
| T (° C.) | 30 | 25 | 18 | 18 |

Initial Conditions:
Initial enantiomeric excess: 9% ee.

| Weight of ethanol (g) | Weight of water (g) | Weight of (±) (g) | Weight of (−) (g) | Weight of potassium hydroxide (g) |
|---|---|---|---|---|
| 160 | 6.4 | 11.6 | 1.15 | 2.57 |

Results:

Filtration through a Büchner funnel (diameter 5 cm, double filter paper)

| Entrainment No. | Weight of pure enantiomer* (g) | Equivalent weight of (S)-omeprazole (g) | Enantiomeric excess (% ee) |
|---|---|---|---|
| 1 | 2.1 | 1.5 | (−) 95.1 |
| 2 | 3.6 | 2.6 | (+) 93.4 |
| 3 | 4.1 | 3.0 | (−) 96.0 |
| 4 | 4.2 | 3.1 | (+) 90.3 |

*The pure enantiomer corresponds to the ethanol solvate of the potassium salt of (S)-omeprazole Mean enantiomeric excess: 94% ee.

Example 3

Resolution in the Ethanol/Water Azeotropic Mixture by Auto-Seeded Preferential Crystallization Conditions Related to the Equilibria:

Solubility of the racemic mixture in the ethanol/water azeotropic mixture comprising 1.2 molar equivalents of potassium hydroxide (i.e., an excess of potassium hydroxide of 0.2 equivalent)

Coordinates of the point L: 13.7% by weight; temperature $T_L$: 35° C.

| Temperature (° C.) | 29 | 31 | 35 |
|---|---|---|---|
| Solubility (% by weight) | 8.7 | 9.1 | 13.7 |

Change in $T_{HOMO}$ with the enantiomeric excess:

| % (−) enantiomer | 0 | 3 | 6 | 9 |
|---|---|---|---|---|
| $T_{HOMO}$ (° C.) | 35 | 36 | 37 | 38 |

Conditions Related to the Kinetics:
Temperature $T_B$: 36° C.
Temperature $T_F$: 25° C.
Cooling kinetics: T=f(t):

| t (min) | 0 | 15 | 30 | 45 |
|---|---|---|---|---|
| T (° C.) | 36 | 30 | 25 | 25 |

Initial Conditions:
Initial enantiomeric excess: 9% ee.

| Weight of ethanol (g) | Weight of water (g) | Weight of (±) (g) | Weight of (−) (g) | Weight of potassium hydroxide (g) |
|---|---|---|---|---|
| 160 | 6.4 | 19 | 1.88 | 4.1 |

Results:

Filtration through a Büchner funnel (diameter 5 cm, double filter paper)

| Entrainment No. | Weight of pure enantiomer* (g) | Equivalent weight of (S)-omeprazole (g) | Enantiomeric excess (% ee) |
|---|---|---|---|
| 1 | 5.9 | 4.3 | (−) 84.1 |
| 2 | 7.0 | 5.1 | (+) 95.8 |
| 3 | 6.2 | 4.5 | (−) 94.0 |
| 4 | 6.1 | 4.4 | (+) 87.0 |

*The pure enantiomer corresponds to the ethanol solvate of the potassium salt of (S)-omeprazole Mean enantiomeric excess: 90% ee.

Example 4

Resolution in an Ethanol/Water Mixture by Auto-Seeded Preferential Crystallization Starting from the mother liquor resulting from entrainment No. 4 of Example 3, compensating is carried out and water is added in order to increase the solubility.

Conditions Related to the Equilibria:

The ethanol/water mixture is estimated at 86/14% weight/weight.

Change in $T_{HOMO}$ with the enantiomeric excess:

| % (−) enantiomer | 0 | 3 | 6 | 9 |
|---|---|---|---|---|
| $T_{HOMO}$ (° C.) | 14 | 16 | 18 | 20 |

Conditions Related to the Kinetics:
Temperature $T_B$: 15° C.
Temperature $T_F$: 2° C.
Cooling of kinetics: T=f(t):

| t (min) | 0 | 15 | 30 | 45 |
|---|---|---|---|---|
| T (° C.) | 15 | 10 | 5 | 2 |

Initial Conditions:
Initial enantiomeric excess: 8.2% ee.

| Weight of ethanol (g) | Weight of water (g) | Weight of (±) (g) | Weight of (−) (g) | Weight of potassium hydroxide (g) |
|---|---|---|---|---|
| 160 | 17.9 | 42.5 | 3.8 | 9.1 |

Results:

Filtration through a Büchner funnel (diameter 5 cm, double filter paper)

| Entrainment No. | Weight of pure enantiomer* (g) | Equivalent weight of (S)-omeprazole (g) | Enantiomeric excess (% ee) |
|---|---|---|---|
| 1 | 6.4 | 4.8 | (−) 75.5 |
| 2 | 8.7 | 7.0 | (+) 80 |
| 3 | 13.2 | 12.3 | (−) 93.2 |
| 4 | 15.6 | 13.1 | (+) 83.9 |

*The pure enantiomer corresponds to the ethanol solvate of the potassium salt of (S)-omeprazole Mean enantiomeric excess: 83% ee.

Example 5

Resolution in an Ethanol/Water (90/10% Weight/Weight) Mixture by Auto-Seeded Preferential Crystallization at a 2 Litre Scale Conditions Related to the Equilibria:

Solubility of the racemic mixture in the ethanol/water (90/10% weight/weight) mixture comprising 1.2 molar equivalents of potassium hydroxide (i.e., an excess of potassium hydroxide of 0.2 equivalent):

Coordinates of the point L: 25% by weight; temperature $T_L$: 30° C.

| Temperature (° C.) | 30 |
|---|---|
| Solubility (% by weight) | 25 |

Change in $T_{HOMO}$ with the enantiomeric excess:

| % (−) enantiomer | 0 | 10 |
|---|---|---|
| $T_{HOMO}$ (° C.) | 30 | 34.2 |

Conditions Related to the Kinetics:

Temperature $T_B$: 31° C.

Temperature $T_F$: 21° C.

Cooling kinetics:

T=−⅓ t+31 (between 0 and 30 minutes, then followed by stationary phase):

| t (min) | 0 | 15 | 30 | 45 |
|---|---|---|---|---|
| T (° C.) | 31 | 26 | 21 | 21 |

Initial Conditions:

Initial enantiomeric excess: 10% ee.

| Weight of ethanol (g) | Weight of water (g) | Weight of (±) (g) | Weight of (−) (g) | Weight of potassium hydroxide (g) |
|---|---|---|---|---|
| 1440 | 160 | 388 + 5.1 (*) | 43.6 | 69.2 |

(*) weight of racemic mixture added subsequent to the addition of enantiomer with an 89.4% ee.

Results:

Filtration takes place on a centrifuge (Rousselet-Robatel France RA20) at 5000 rpm with a basket with a diameter of 200 mm and a height of 100 mm, the pore diameter of the nylon filtering media being 20 μm.

| Entrain-ment No. | Weight of pure enantiomer* (g) | Equivalent weight of (S)-omeprazole (g) | Enantiomeric excess (% ee) | Ethanol compen-sation |
|---|---|---|---|---|
| 1 | 125.2 | 90.9 | (+) 89.4 | — |
| 2 | 126.4 | 91.8 | (−) 97.2 | — |
| 3 | 157.7 | 114.5 | (+) 87.6 | — |
| 4 | 160.8 | 116.8 | (−) 94.6 | — |
| 5 | 222.7 | 161.7 | (+) 96.8 | — |

*The pure enantiomer corresponds to the ethanol solvate of the potassium salt of (S)-omeprazole. The weight given in this column is equal to the weight of the crystals harvested multiplied by the enantiomeric excess.

Mean enantiomeric excess: 93.1% ee.

Example 6

Resolution in an Ethanol/Water (93/7% Weight/Weight) Mixture by Auto-Seeded Preferential Crystallization at a 2 Litre Scale Conditions Related to the Equilibria:

Solubility of the racemic mixture in the ethanol/water (93/7% weight/weight) mixture comprising 1.2 molar equivalents of potassium hydroxide (i.e., an excess of potassium hydroxide of 0.2 equivalent):

Coordinates of the point L: 20% by weight; temperature $T_L$: 34.4° C.

Change in $T_{HOMO}$ with the enantiomeric excess:

| % (−) enantiomer | 0 | 8.4 |
|---|---|---|
| $T_{HOMO}$ (° C.) | 34.4 | 37.1 |

Conditions Related to the Kinetics:

Temperature $T_B$: 35° C.

Temperature $T_F$: 25° C.

Cooling kinetics:

T=−⅓ t+35 (between 0 and 30 minutes, then followed by stationary phase):

| t (min) | 0 | 15 | 30 | 45 |
|---|---|---|---|---|
| T (° C.) | 35 | 30 | 25 | 25 |

Initial Conditions:

Initial enantiomeric excess: 8.3% ee.

| Weight of ethanol (g) | Weight of water (g) | Weight of (±) (g) | Weight of (−) (g) | Weight of potassium hydroxide (g) |
|---|---|---|---|---|
| 1440 | 110 | 271 | 24.8 | 55 |

Results:

Filtration takes place on a centrifuge (Rousselet-Robatel France RA20) at 5000 rpm with a basket with a diameter of 200 mm and a height of 100 mm, the pore diameter of the nylon filtering media being 20 μm.

| Entrainment No. | Weight of pure enantiomer* (g) | Equivalent weight of (S)-omeprazole (g) | Enantiomeric excess (% ee) | Ethanol compensation (g) |
|---|---|---|---|---|
| 1 | 98.36 | 71.44 | (+) 89.4 | 45 |
| 2 | 119.59 | 86.86 | (−) 97.2 | — |
| 3 | 138.41 | 100.53 | (+) 87.6 | — |
| 4 | 132.40 | 96.16 | (−) 94.6 | 50 |
| 5 | 106.50 | 77.34 | (+) 96.8 | — |
| 6 | 133.30 | 96.82 | (−) 95.2 | — |
| 7 | 129.37 | 93.97 | (+) 93.8 | — |

*The pure enantiomer corresponds to the ethanol solvate of the potassium salt of (S)-omeprazole. The weight given in this column is equal to the weight of the crystals harvested multiplied by the enantiomeric excess Mean enantiomeric excess: 93.5% ee.

Example 7

Resolution in Ethanol by Auto-Seeded Preferential Crystallization

Conditions Related to the Equilibria:

Solubility of the racemic mixture in absolute ethanol comprising 1.2 molar equivalents of potassium hydroxide (i.e., an excess of potassium hydroxide of 0.2 equivalent)

Coordinates of the point L: 2.2% by weight; temperature $T_L$: 33° C.

| Temperature (° C.) | 26 | 30 | 33 |
|---|---|---|---|
| Solubility (% by weight) | 1.3 | 1.7 | 2.2 |

Change in $T_{HOMO}$ with the enantiomeric excess:

| % (−) antipode | 0 | 3 | 6 | 9 |
|---|---|---|---|---|
| $T_{HOMO}$ (° C.) | 33.0 | 33.2 | 33.5 | 33.8 |

Conditions Related to the Kinetics:
Temperature $T_B$: 33.2° C.
Temperature $T_F$: 13° C.
Cooling kinetics: T=f(t):

| t (min) | 0 | 30 | 45 | 60 |
|---|---|---|---|---|
| T (° C.) | 33.2 | 15 | 13 | 13 |

Initial Conditions:
Initial enantiomeric excess: 9% ee.

| Weight of ethanol (g) | Weight of (±) (g) | Weight of (−) (g) | Weight of potassium hydroxide (g) |
|---|---|---|---|
| 160 | 2.58 | 0.256 | 0.51 |

The resolution in ethanol shows the poorest results; consequently, its study was not continued and no filtration was carried out. This is because the time necessary for each entrainment operation is of the order of 3 hours. The solubility of the salt is low and the crystal harvest thus obtained is low, of the order of 2.5 g per 1 l of solution, which is harmful to the yield of each entrainment.

Example 8

Resolution in the Ethanol/Ethylene Glycol (80/20% Weight/Weight) Mixture by Auto-Seeded Preferential Crystallization Conditions Related to the Equilibria:
Change in $T_{HOMO}$ with the enantiomeric excess:

| % (−) enantiomer | 0 | 3.2 | 6 | 9 |
|---|---|---|---|---|
| $T_{HOMO}$ (° C.) | 33.3 | 34.3 | 35.1 | 35.6 |

Conditions Related to the Kinetics:
Temperature $T_B$: 35° C.
Temperature $T_F$: 18° C.
Cooling kinetics: T=f(t):

| t (min) | 0 | 20 | 30 | 40 | 45 |
|---|---|---|---|---|---|
| T (° C.) | 35 | 28 | 24 | 20 | 18 |

Initial Conditions:
Initial enantiomeric excess: 9% ee.

| Weight of ethanol (g) | Weight of ethylene glycol (g) | Weight of (±) (g) | Weight of (−) (g) | Weight of potassium hydroxide (g) |
|---|---|---|---|---|
| 32 | 8 | 10.35 | 0.74 | 2.14 |

Results:
Filtration through sintered glass No. 3

| Entrainment No. | Weight of pure enantiomer* (g) | Enantiomeric excess (% ee) |
|---|---|---|
| 1 | 2.9 | (−) 70.0 |
| 2 | 2.3 | (+) 62.5 |
| 3 | 2.7 | (−) 63.8 |
| 4 | 3.5 | (+) 78.0 |

*The pure enantiomer corresponds to a mixture between the ethanol solvate of the potassium salt of (S)-omeprazole and the ethylene glycol solvate of the potassium salt of (S)-omeprazole Mean enantiomeric excess: 68.6% ee.

Example 9

Structure of the Potassium Salt of (S)-Omeprazole Solvated with Ethanol

A single crystal was obtained in a saturated solution of racemic omeprazole prepared by dissolution of racemic omeprazole in an ethanolic potassium hydroxide solution. The nucleation and then the growth of the single crystal were induced by reducing the temperature, bringing about supersaturation in salt of the solution.

The crystal structure of the single crystal was solved in the monoclinic system, space group $P2_1$. The crystal unit cell comprises one molecule of omeprazole in the anionic form, one potassium cation and two ethanol molecules.

The diffraction intensities were measured with an automatic Smart Apex diffractometer (Bruker) provided with SMART software (SMART for WNT/2000 V5.622 (2001), Smart software reference manual, Bruker Advanced X Ray Solutions Inc., Madison, Wis., USA) and the structure was solved with SAINT+, SADABS and SHELXS software (SAINT+ V6.02 (1999), Saint software reference manual, Bruker Advanced X Ray Solutions Inc., Madison, Wis., USA).

The reliability factor R1 is 3.09%, which indicates that the resolution is satisfactory. The value of the Flack parameter is 0.11, which allows it to be concluded that the molecule, in the crystal studied, is indeed of (S) absolute configuration.

The crystallographic characteristics of this phase are collated in the following Table V.

TABLE V

| Identification | Potassium salt of (S)-omeprazole solvated with 2 molecules of ethanol |
|---|---|
| Chemical formula | $C_{21}H_{30}KN_3O_5S_1$ |
| Molar mass (g · mol$^{-1}$) | 475.64 |
| Crystal system | Monoclinic |
| Space group | $P2_1$ |
| Z, Z' | 2, 1 |
| a (Å) | 11.057 |
| b (Å) | 7.708 |
| c (Å) | 13.989 |
| α (°) | 90.0 |
| β (°) | 100.12 |
| γ (°) | 90.0 |
| V (Å$^3$) | 1173.8 |

The 3D representation of the asymmetric unit using Diamond software is presented in FIG. 6 and reveals: the benzimidazole anion, the potassium cation and 2 ethanol molecules. There is no direct electrostatic connection between the nitrogen atoms of the benzimidazole ring system and the K$^+$ cation. The connection is made via the intermediary of an ethanol molecule.

The coordinates of the atoms in the crystal unit cell are presented in Table VI below.

TABLE VI

Atomic coordinates (×10$^4$) and isotropic displacement parameters (Å$^2$ × 10$^3$)

| | x | y | z | U(eq) |
|---|---|---|---|---|
| K (1) | 10723 (1) | 7414 (1) | 10034 (1) | 40 (1) |
| S (1) | 7268 (1) | 6353 (1) | 10330 (1) | 32 (1) |
| N (1) | 9493 (2) | 9468 (2) | 11377 (1) | 37 (1) |
| O (4) | 13316 (1) | 7340 (3) | 10314 (1) | 48 (1) |
| C (8) | 5798 (2) | 7542 (3) | 7719 (1) | 36 (1) |
| N (3) | 6824 (1) | 7257 (3) | 8417 (1) | 38 (1) |
| O (5) | 9024 (2) | 9070 (3) | 8606 (1) | 55 (1) |
| C (10) | 8449 (2) | 8839 (2) | 11601 (1) | 32 (1) |
| O (1) | 9268 (2) | 8297 (3) | 14226 (1) | 62 (1) |
| C (16) | 8317 (2) | 8429 (3) | 12556 (1) | 37 (1) |
| C (17) | 7142 (2) | 7704 (4) | 12789 (2) | 53 (1) |
| N (2) | 5106 (1) | 6797 (2) | 9104 (1) | 38 (1) |
| C (2) | 4742 (2) | 7272 (3) | 8141 (1) | 36 (1) |
| C (3) | 3573 (2) | 7525 (4) | 7593 (2) | 49 (1) |
| C (5) | 4528 (2) | 8288 (3) | 6221 (2) | 48 (1) |
| C (12) | 10435 (2) | 9342 (3) | 13063 (2) | 45 (1) |
| C (7) | 5695 (2) | 8044 (3) | 6747 (2) | 47 (1) |
| O (3) | 4283 (2) | 8785 (3) | 5261 (1) | 71 (1) |
| C (4) | 3484 (2) | 8034 (3) | 6640 (2) | 51 (1) |
| C (14) | 9334 (2) | 8712 (3) | 13279 (1) | 42 (1) |
| C (13) | 11563 (2) | 9610 (5) | 13825 (2) | 69 (1) |
| C (11) | 10450 (2) | 9701 (3) | 12099 (2) | 40 (1) |
| C (21) | 9206 (2) | 9536 (5) | 7663 (2) | 69 (1) |
| C (20) | 10438 (3) | 9094 (4) | 7475 (2) | 61 (1) |
| C (6) | 5298 (3) | 8970 (6) | 4771 (2) | 81 (1) |
| C (18) | 13537 (3) | 7470 (6) | 12043 (2) | 79 (1) |
| C (19) | 14043 (2) | 6936 (5) | 11210 (2) | 75 (1) |
| C (15) | 8819 (4) | 9683 (6) | 14746 (2) | 90 (1) |
| O (2) | 8510 (1) | 5858 (2) | 10129 (1) | 39 (1) |
| C (1) | 6326 (2) | 6841 (2) | 9189 (1) | 32 (1) |
| C (9) | 7425 (2) | 8611 (3) | 10747 (1) | 36 (1) |

The experimental X-ray powder diffractograms of the racemic and enantiomerically pure phases and the X-ray powder diffractogram calculated from this structure are presented in FIG. 4.

Example 10

Preparation of the Potassium Salt of (S)-Omeprazole from the magnesium salt of (S)-Omeprazole (S)-Omeprazole magnesium salt trihydrate (10.02 g), which is available commercially, is dissolved in 400 ml of ethanol, to which potassium hydroxide is added in excess (3.99 g, 2.5 molar equivalents). The potassium salt is crystallized by partial evaporation of the solvent and then filtered on a Büchner funnel. The product obtained (14.7 g) is recrystallized from 2 liters of ethanol at 45° C. A hot filtration is carried out in order to remove the impurities which are insoluble in the presence of potassium hydroxide (0.87 g, approximately 0.5 molar equivalent).

Example 11

Enantiomeric Purification 10.2 g (out of the 10.88 g of crystals harvested) of potassium salt of (S)-omeprazole (80% ee, i.e. a weight of pure (S) enantiomer of 8.16 g) obtained by the entrainment No. 2 of Example 4 are suspended in 120 g of ethanol with stirring and thermostatically controlled at 25° C., and are treated with an excess of potassium hydroxide (0.11 g, 0.1 molar equivalent).

The temperature is gradually reduced until the optical rotation of the mother liquor is close to zero. The solid obtained is filtered off on a Büchner funnel. After drying, the weight of the potassium salt recovered is 7.7 g (for 8.16 g theoretically recoverable), i.e. a yield of greater than 94%, with an enantiomeric purity of greater than 99% ee (measured by chiral HPLC chromatography).

Example 12

Enantiomeric Purification

The crystals harvested from the resolution operations:
Example 6 entrainment 2 (−): 119 g (97% ee, i.e. 115 g of (−) enantiomer);
Example 6 entrainment 4 (−): 135 g (94% ee, i.e. 126 g of (−) enantiomer);
Example 6 entrainment 6 (−): 133 g (95% ee, i.e. 126 g of (−) enantiomer),
i.e. 387 g in total, that is to say 367 g of (−) enantiomer, were mixed and suspended in 2 liters of an ethanolic potassium hydroxide solution, so that the amount of potassium hydroxide corresponds to 0.1 molar equivalent with respect to the omeprazole (=4.5 g; the starting ethanol was absolute ethanol).

The temperature is brought to 50° C. for half an hour and then is brought rapidly back to 30° C. and slowly as far as 14° C., the change in the optical rotation of the mother liquor being monitored by polarimetry.

When the three-phase region is reached (i.e., the optical rotation is zero), the temperature is raised to 16° C. for 12 hours in order to achieve thermodynamic equilibrium in the two-phase region (diethanolate of the potassium salt of the (−) enantiomer of omeprazole and its saturated solution). Once at equilibrium, the temperature is lowered to 13° C. in order to have an entrainment effect and to recover a greater weight of enantiomer.

After ½ hour, filtration takes place on a centrifuge (Rousselet-Robatel France RA20) at 5000 revolutions/min with a basket with a diameter of 200 mm and a height of 100 mm, the pore diameter of the nylon filtering medium of which is 20 μm.

The weight of crystals harvested is 352 g.
An HPLC analysis was carried out in order to measure the optical purity of the sample after recrystallization.
The purity is 99.4% ee and the yield is 95%.

Example 13

Preparation of the Ethylene Glycol Solvate of the Potassium Salt of Racemic Omeprazole Racemic omeprazole (1.01 g) is dissolved in a mixture of methanol and ethylene glycol (respectively 4 ml and 1 ml) in the presence of potassium hydroxide (180 mg, 1.1 molar equivalents). After stirring at ambient temperature for 3 hours, the solid is recovered by filtration on a Büchner funnel. The solid obtained corresponds to a mixture of phases between the methanol solvate and the ethylene glycol solvate of the potassium salt of racemic omeprazole. After drying, the methanol solvate becomes amorphous; the only phase observed by X-ray powder diffraction is the ethylene glycol solvate. The diffractogram (XRPD) is presented in FIG. 5.

Example 14

Preparation of the Ethylene Glycol Solvate of the Potassium Salt of (S)-Omeprazole The ethanol solvate of the potassium salt of (S)-omeprazole (3.01 g), obtained by recrystallization of the crystals harvested from entrainment 1 of Example 4 by the same protocol as in Example 12, is suspended in a mixture of solvents composed of methanol and ethylene glycol (2 ml and 1 ml respectively). After stirring at ambient temperature for 5 days, the suspension is recovered by filtration on a sintered glass No. 3. The solid obtained is a mixture of phases between the methanol solvate and the ethylene glycol solvate of the potassium salt of (S)-omeprazole. After drying under an ambient atmosphere, methanol solvate becomes amorphous; the only phase observed by X-ray powder diffraction is the ethylene glycol solvate. The diffractogram (XRPD) is presented in FIG. 5.

The invention claimed is:

1. A method for the resolution of salts of racemic omeprazole, comprising:
converting racemic omeprazole to potassium salt in the form of solvates in the presence of an excess of inorganic base which is a source of potassium, the said potassium salts of racemic omeprazole in the form of solvates existing in the form of conglomerates, the partial solid solution regions of which, if they exist, are less than 1%; and
resolving the said conglomerates by preferential crystallization in order to separate the two (S) and (R) enantiomers of the said potassium salt of racemic omeprazole.

2. The method according to claim 1, wherein the solvates of the potassium salt of racemic omeprazole are chosen from: the ethanol solvate or the ethylene glycol solvate or a mixture of these.

3. The method according to claim 1, wherein the conglomerates are resolved by seeded or auto-seeded preferential crystallization.

4. The method according to claim 1, wherein the preferential crystallization is carried out with a system selected from the group consisting of:
quinary systems [$K_2O$-EtOH—$H_2O$-(−)-omeprazole-(+)-omeprazole] and [$K_2O$-ethylene glycol-$H_2O$-(−)-omeprazole-(+)-omeprazole];
a senary system [$K_2O$-EtOH-ethylene glycol-$H_2O$-(−)-omeprazole-(+)-omeprazole]; and
ternary systems, by classification of the quinary systems as ternary systems comprising the constituents: alcohol(s) (ethanol and/or ethylene glycol), water and excess of potassium hydroxide in the medium.

5. The method according to claim 1, wherein the preferential crystallization is seeded and comprises the following stages:
a) a first homogeneous solution is prepared which is composed of the racemic mixture in the conglomerate form and of an excess of the first enantiomer to be recovered in the form of a solvate of the potassium salt of (X)-omeprazole, denoted X—K-solvate, where X represents the (R) or (S) enantiomer, and of a medium, the representational point I of which, defined by the variables of concentration and temperature $T_I$ ($T_I > T_{HOMO}$) lies within the single-phase region composed of the under-saturated solution;
b) a cooling programming law is applied to the single-phase mixture;

c) when the mixture reaches a temperature below the temperature $T_{HOMO}$, the solution is seeded with enantiomerically pure seeds of the first X—K-solvate enantiomer to be recovered;

d) throughout the duration of the crystal growth, a stirring rate which gently increases as a function of the time is adjusted so that it is sufficiently slow to promote growth of the first X—K-solvate enantiomer;

e) the crystals of the first X—K-solvate enantiomer are harvested;

f) the same weight of racemic mixture as the weight of the crystals harvested in the preceding stage is added to the mother liquors and the new combination is brought to the temperature $T_I$ ($T_I > T_{HOMO}$) the point I' lying in the single-phase region;

g) the same cooling programming law as in stage (b) is applied to the single-phase mixture prepared in stage (f) comprising the second enantiomer, so that the mother liquors retain a slight supersaturation during the crystallization in order to favour the growth of the second X—K-solvate enantiomer during the seeding;

h) when the mixture reaches a temperature below the temperature $T_{HOMO}$, the solution is seeded with enantiomerically pure seeds of the second X—K-solvate enantiomer;

i) throughout the duration of the crystal growth of the preceding stage, a stirring rate which gently increases as a function of the time is adjusted so that it is sufficiently slow to promote the growth of this second X—K-solvate enantiomer;

j) the crystals of the second X—K-solvate enantiomer are harvested;

k) the same weight of racemic mixture as the weight of the crystals harvested in the preceding stage is added to the mother liquors in order to obtain a solution having an identical composition to that of the initial solution; and l) stages (a) to (k) are repeated in order to successively obtain one and then the other of the two enantiomers.

6. The method according to claim 1, wherein the preferential crystallization is auto-seeded and comprises the following stages:

a) a first combination is prepared which is composed of the racemic mixture in the conglomerate form, of the first enantiomer to be recovered, in the form of a solvate of the potassium salt of (X)-omeprazole, denoted X—K-solvate, where X represents the (R) or (S) enantiomer, and of a medium, the representational point E of which, defined by the variables of concentration and temperature $T_B$, lies within the two-phase region composed of crystals of X—K-solvate and of its saturated solution;

b) a cooling programming law is applied to the two-phase mixture, such that the mother liquors retain a slight supersaturation which favours the growth of the first X—K-solvate enantiomer present in the form of crystals, while preventing the spontaneous nucleation of the second X—K-solvate enantiomer dissolved in the solution;

c) throughout the duration of the crystal growth, a stirring rate which gently increases as a function of the time is adjusted so that it is sufficiently slow to promote growth of the first X—K-solvate enantiomer, while avoiding the generation of uncontrolled nucleation and the attrition of crystals;

d) the crystals of the first X—K-solvate enantiomer are harvested;

e) the same weight of racemic mixture as the weight of the crystals harvested in the preceding stage is added to the mother liquors and the new combination is brought to the temperature $T_B$, the point E' lying in the two-phase region of the second X—K-solvate enantiomer in excess, in equilibrium with its saturated solution;

f) the same cooling programming law as in stage (b) is applied to the two-phase mixture prepared in stage (e) comprising the second X—K-solvate enantiomer, so that the mother liquors retain a slight supersaturation during the crystallization, in order to favour the growth of the second X—K-solvate enantiomer present in the form of crystals, while preventing the spontaneous nucleation of the first X—K-solvate enantiomer present in the solution;

g) throughout the duration of the crystal growth of the preceding stage, a stirring rate which gently increases as a function of the time is adjusted so that it is sufficiently slow to promote the growth of this second X—K-solvate enantiomer while avoiding the generation of uncontrolled nucleation and the attrition of crystals;

h) the crystals of the second X—K-solvate enantiomer are harvested;

i) the same weight of racemic mixture as the weight of the crystals harvested in the preceding stage is added to the mother liquors in order to obtain a combination having an identical composition to that of the initial combination E;

j) stages (a) to (i) are repeated in order to successively obtain one and then the other of the two enantiomers.

7. The method according to claim 5, wherein, in stage (a), the medium is composed of an alcoholic solvent or mixture of alcoholic solvents, water and an excess of potassium hydroxide.

8. The method according to claim 7, wherein the alcoholic solvent or the mixture of alcoholic solvents is chosen from ethanol or ethylene glycol, pure or in the presence of water.

9. The method according to claim 1, further comprising a stage of recycling the (R) enantiomer according to the following stages:

i) Reduction of this chiral (R) sulphoxide to give the achiral sulphide (thioether), and ii) Oxidation of the sulphur atom of this sulphide to give the racemic sulphoxide, using aqueous hydrogen peroxide solution or hypochlorite ion or perbenzoic acid or any other oxidizing agent, while avoiding the formation of sulphone.

10. The method according to claim 6, wherein, in stage (a), the medium is composed of an alcoholic solvent or mixture of alcoholic solvents, water and an excess of potassium hydroxide.

11. The method according to claim 10, wherein the alcoholic solvent or the mixture of alcoholic solvents is chosen from ethanol or ethylene glycol, pure or in the presence of water.

* * * * *